United States Patent [19]

Jutard et al.

[11] Patent Number: 5,598,262
[45] Date of Patent: Jan. 28, 1997

[54] PROCESS AND DEVICE FOR INSPECTING TRANSPARENT MATERIAL

[75] Inventors: Yann Jutard, Rennes; Jean-Jacques Sacre, Chateaugiron, both of France

[73] Assignee: Thomson-CSF, Paris, France

[21] Appl. No.: 325,172

[22] PCT Filed: Oct. 13, 1993

[86] PCT No.: PCT/FR93/01015

§ 371 Date: Apr. 20, 1995

§ 102(e) Date: Apr. 20, 1995

[87] PCT Pub. No.: WO94/09358

PCT Pub. Date: Apr. 28, 1994

[30] Foreign Application Priority Data

Oct. 20, 1992 [FR] France .................. 92 12526

[51] Int. Cl.$^6$ .................................................. G01N 21/89
[52] U.S. Cl. .................... 356/239; 348/131; 250/559.41; 250/559.46
[58] Field of Search ...................... 356/237, 239; 250/559.41, 559.42, 559.45, 559.46; 348/125, 127, 131

[56] References Cited

U.S. PATENT DOCUMENTS 2,042,526  6/1936  Hohmann ................... 356/239
3,519,362  7/1970  Cardno et al. ............... 356/237

FOREIGN PATENT DOCUMENTS 342127   11/1989  European Pat. Off. ........... 356/239
3611574  10/1987  Germany ..................... 356/239

*Primary Examiner*—P. L. Evans
*Attorney, Agent, or Firm*—Oblon, Spivak, McClelland, Maier & Neustadt, P.C.

[57] ABSTRACT

The inspection method, in order to detect and locate defects (5) included within the thickness of the transparent material (2) to be inspected, consists in uniformly illuminating a bright background (7) placed relative to the camera (4) behind the material (2) in order to be viewed by transparency through the material (2), covering the field of view of the camera (4) and serving as contrast reference, in laterally illuminating the surface of the material (2) in order to distinguish defects (5) included within the material (2) from parasitic elements (11) deposited on its surface, in viewing by transparency, by the camera (4), placed in the vertical to the surface of the material (2), a sequence of contrasted images reproducing the thickness of the material (2), and in processing information acquired by the successive images which are representative of the material (2) seen in its thickness in order to detect and locate the defects (5) included within the thickness of the material (2).

19 Claims, 2 Drawing Sheets

PROCESS AND DEVICE FOR INSPECTING TRANSPARENT MATERIAL

The present invention relates to a method and a device for inspecting transparent material and concerns the field of automatic industrial inspection by imaging at the exit from a production line.

In a general way, the inspection of a transparent material such as glass, for example, is intended to detect and to locate defects, also called "inclusions", which are generated in the course of the manufacturing phase of the glass. The impact of these defects on the quality of the glass produced depends upon their number, their shape and on the standards imposed on the glassmaker according to the application envisaged.

These defects are of various types, the main ones of which are of the blister type and of the stone type:

In the blister type, the defects are gas bubbles which have remained captive in the material when molten and the shape of which varies from a sphere to a very elongate filament having an aspect ratio exceeding ten.

In the stone type, the defects are defects of homogeneity of the basic constituents, entailing the formation of a visible particle in the glass.

The size and the shape of these inclusions vary depending on the material and the depth within the material. Their size is, in general, less than one millimetre, the maximum resolution reaching one tenth of a millimetre.

The automatic analysis of the quality of the material, i.e. the automatic detection of the defects of the material, reacts directly on its production. This analysis makes it possible to reject the defective products, but also to have reliable statistics available concerning the number and the size of the defects, in order consequently to modify the various production parameters of the material.

Known inspection devices make use of an observation system including a light source, for example a laser source, illuminating a transparent material to be inspected. After passing through the material, the light radiation is analysed by a detection device which is sensitive to the light radiation, for example a CCD camera, and permits the detection and the location, in depth, of any possible defects.

However, the use of artificial vision for the inspection of transparent materials and of glass in particular, is currently limited by a lack of effectiveness concerning the discrimination between surface perturbations, such as dust particles deposited on the surface of the material to be inspected, and inclusions which are actual defects of manufacture which are embedded within the mass of the material. In fact, the presence of dust particles on the surface of the material gives rise to confusion when an actual defect is localized within the mass of the material in proximity to the surface. The dust particles are illuminated in proximity to the light source, and may mask a possible defect situated in proximity to the surface.

On the other hand, certain defects of elongate form do not sparkle when they encounter the light beam and therefore are not detected.

The object of the invention is to alleviate the aforementioned disadvantages.

To this end, the object of the invention is a method for inspecting transparent material by illumination by means of at least one light source, and by observation of the thickness of the material by at least one camera, characterized in that it consists in uniformly illuminating a bright background placed relative to the camera behind the material so as to be viewed by transparency through the material, covering the field of view of the camera and serving as contrast reference, in laterally illuminating the surface of the material in order to distinguish defects included within the material from parasitic elements deposited on its surface, in viewing by transparency by the camera, placed in the vertical to the surface of the material, a sequence of contrasted images reproducing the thickness of the material, and in processing information acquired by the successive images which are representative of the material seen in its thickness, in order to detect and locate the defects included within the thickness of the material.

The subject of the invention is also an inspection device intended for carrying out the method as described above.

The advantage of the invention is that of discriminating the defects embedded within the mass of the material in proximity to the surface from the parasitic surface elements, such as dust particles. The invention likewise allows the defects to be located irrespective of what their shape and their orientation may be, and further permits the measurement of their depth within the material.

Other features and advantages of the invention will become evident hereinbelow with the aid of the description which follows, which is given with reference to the accompanying drawings, in which.

In these figures, the corresponding elements are designated by the same reference.

Figure 1:
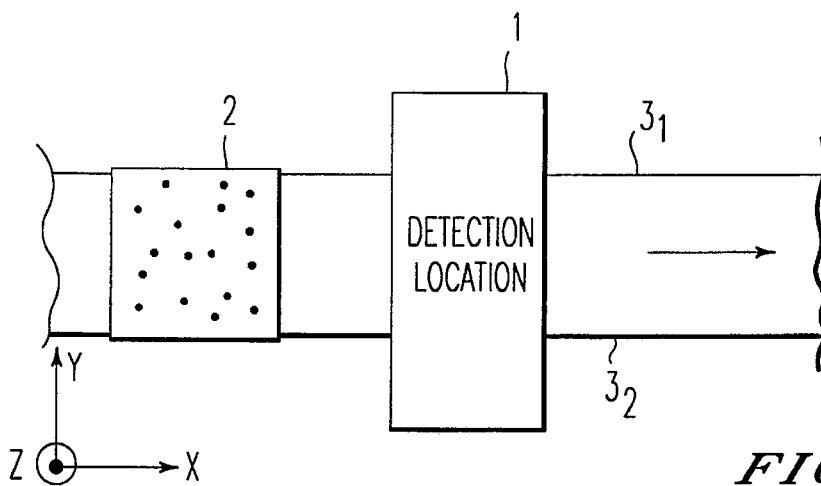
FIG. 1 represents a general view of an inspection device according to the invention.

The inspection device according to the invention, in an embodiment diagrammatically illustrated in a top view in FIG. 1, includes a station 1 for detecting and locating the defects in the three dimensions X, Y, Z. A transparent material 2 is placed on a conveyor, constituted for example by two parallel rails $3_1$ and $3_2$ supporting the material 2, and it is inspected progressively as it passes in the vertical to the station 1 for detecting and locating defects, the movement of the conveyor taking place along the axis X in the direction indicated by the arrow. The station 1 provides one or more images (not shown) of the successive sections of the material 2.

Figure 2:
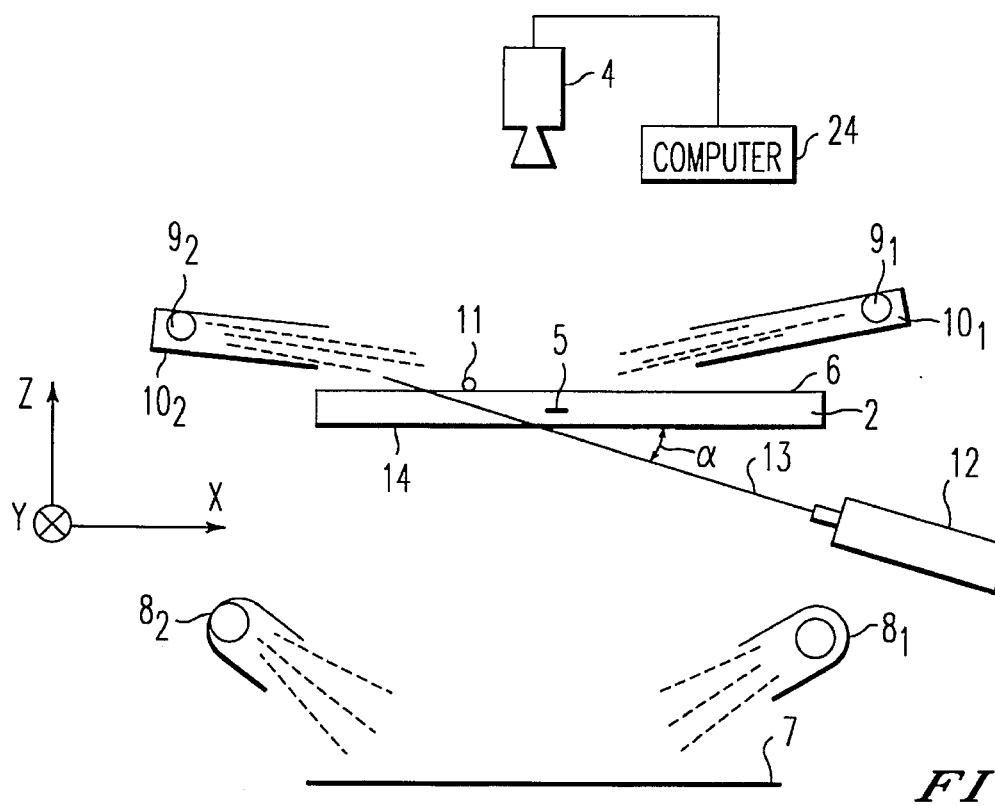
FIG. 2 represents a side view of an embodiment of the device according to the invention.

A side view of an embodiment of the device according to the invention is illustrated by FIG. 2. In this figure, the conveyor $3_1$ and $3_2$ is not shown. The device includes a black and white camera 4 utilizing, for example, sensors of CCD type, observing by transparency the material 2 to be inspected. Depending upon the optical system which is attached to it, the camera 4 covers a variable zone of the material with a given resolution. The adjustment of the lens of the camera 4 forms the subject of a compromise between the depth of field covering the thickness of the material 2 of the order of a few millimetres and the magnification ensuring the detection of the defects 5 with a maximum resolution of the order of one tenth of a millimetre.

The camera 4 is placed perpendicular to the upper surface 6 of the material 2.

A weakly illuminated bright background 7 is placed set back beneath the material 2. The camera 4 covers the zone of observation of the material corresponding to a section within the thickness of the material 2 and does not receive direct light emanating from the illumination of the bright background 7. In order to obtain a uniform illumination over the background 7, neon tubes, $8_1$ and $8_2$ for example, are placed around the bright background 7 which thus diffuses the light received on its surface. It may be constructed, for example, of white paper. This bright background 7 in fact forms a plane, the uniform contrast of which serves as contrast reference. Thus, in the example of the white paper background, the camera 4 reproduces an entirely white image corresponding to a section of the transparent material 2 without defect. On the other hand, any defect 6 present within the mass of the material 2 is perceived as a dark spot on the bright background 7.

A grazing-beam illumination source $9_1$ and $9_2$, for example of white light, is disposed laterally to the material 2. The orientation of the light rays incident on the upper surface 6 of the material 2 is determined in such a manner that they exhibit almost no penetration into the material 2, thus avoiding illumination of defects 5 included in proximity to the surface 6. The illumination is, for example, provided by low-power neon tubes. They are placed within a device $10_1$ and $10_2$ so that the light rays all emerge virtually parallel to one another. The device $10_1$ and $10_2$ is, for example, composed of two plane surfaces placed parallel, serving as optical guide for the light rays. The purpose of this illumination is to illuminate the upper surface 6 of the material 2. Thus, everything which is situated at the surface within the field of view of the camera 4 is illuminated and sends an excess light intensity towards the camera 4.

The grazing illumination may also use a light source, of which the wavelength of the incident rays delivered by the source is such that they do not penetrate into the material of given refractive index. In that case, the detectors of the camera are adapted to detect these wavelengths. Dust particles 11 deposited on the upper surface 6 of the material 2 are expressed, in the image reconstructed by the camera 4, either as brighter points, for example white points, standing out from the bright background 7, which may be slightly greyish, serving as contrast reference, or embedded within the background 7.

A light source 12 of laser type, for example a helium neon laser, is placed beneath the material 2 to be inspected, centered between the two rails $3_1$ and $3_2$ between the material 2 and the bright background 7, and emits a beam 13 forming a specified angle, $\alpha$, between the lower face 14 of the material 2 and the beam 13. The laser source 12 is coupled to a known beam expansion means, not shown. This means is, for example, composed of an optical bar in such a manner as to spread the laser beam 13 emitted by the source 12 in one single direction. The inclined arrangement of the laser source 12 in relation to the lower face 14 of the material 2 permits the utilization of only a single camera 4 in the case in which the material 2 is not flat, but slightly convex.

Figure 3:
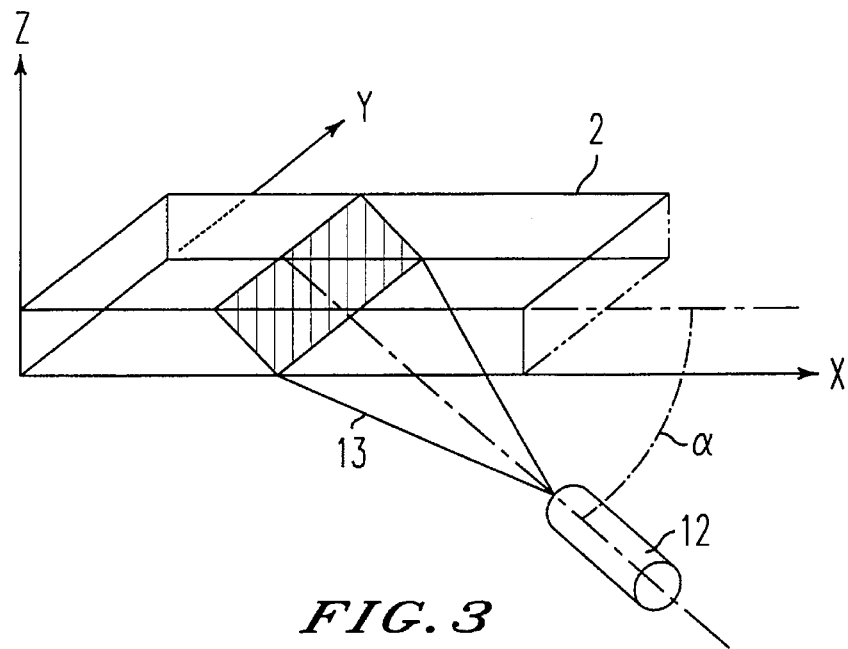
FIG. 3 represents a detailed view of the device according to the invention.

FIG. 3 represents a partial perspective view of the preceding embodiment representing, in the reference system X-Y-Z, the material 2 illuminated by the laser source 12. The laser beam 13 thus shaped by the aforementioned optical means forms a light curtain, represented by a hatched zone, of matched thickness, which corresponds at each instant to an oblique section of the material 2.

Figure 4:
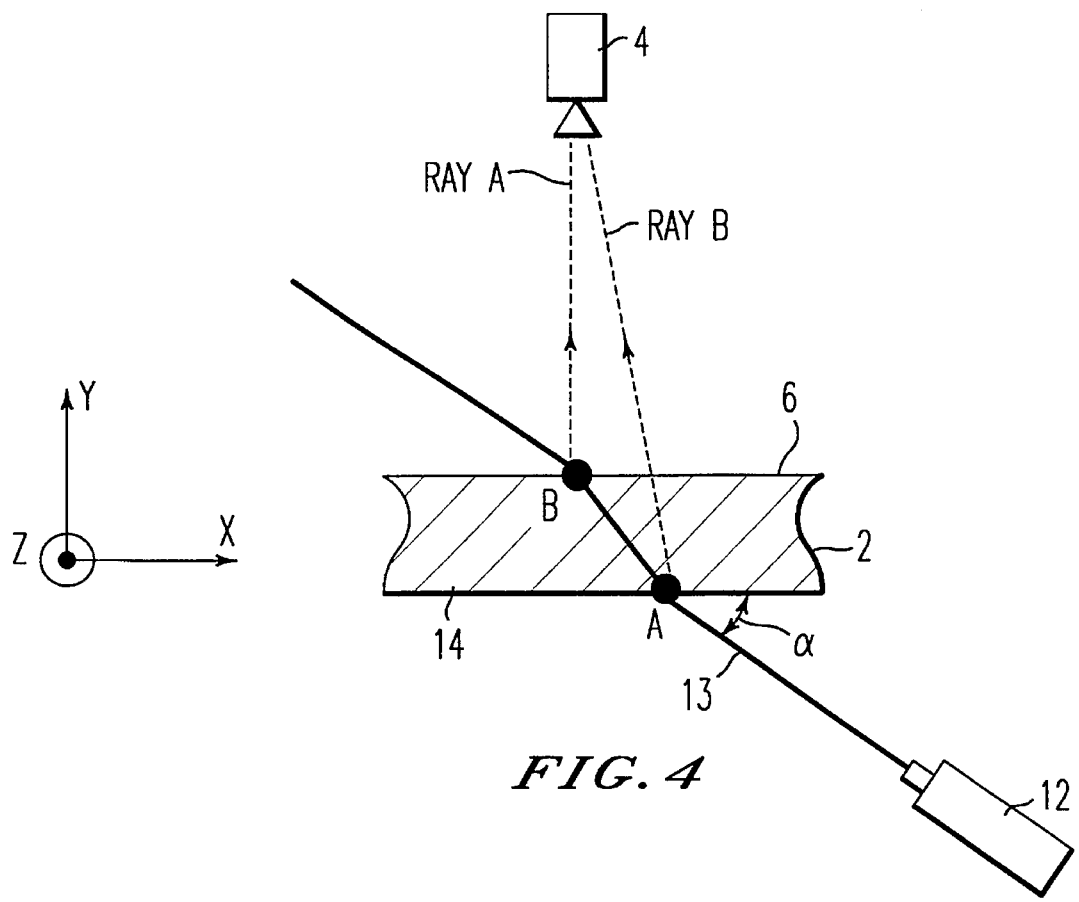
FIG. 4 represents an optical diagram.

FIG. 4 illustrates a partial section of the material 2 and the position of the laser 12 in relation to the material 2. The laser beam 13 emitted by the laser source 12 passes right through the thickness of the transparent material 2, and forms an angle $\alpha$ with the lower face 14 of the material 2. Each face 6 and 14 of the material 2, which face is thus traversed by the laser beam 13 at the points A and B respectively, is expressed, on the image, by a horizontal stroke or a curved line following the curvature of the material, in excess brightness in relation to the background 7. The distance between each one of these strokes serves as reference for the calculation of the depth of the defects 5 within the thickness of the material 2 delimited by the two strokes. Thus, the height of the sectional plane of the material viewed by the camera 4 within the material 2 is given by the segment AB represented as the intersection of the laser beam 13 with the transparent material 2. The rays a and b are represented in FIG. 4 by dotted lines and are the rays, emanating from the laser beam 13, which are generated by scattering at each air/material interface, 13, and material/air interface, 6, and detected by the camera 4. Being thus scattered, they avoid a dazzling of the camera 4. On the other hand, this arrangement without nevertheless excessively absorbing the radiation, permits the avoidance of multiple reflections in the visible spectrum. The inclination by the angle $\alpha$ of the laser source 12 further permits the increasing of the resolution of the measurement in depth of the defects 5, the segment AB being longer as compared with a segment vertically cutting the thickness of the material 2. The angle $\alpha$ is, for example, 45°; beyond that, the resolution with respect to the relative error of the measurement of the depth of the defect 5 diminishes.

The information supplied by the station 1 permits locating, by imaging, of the defect in the three dimensions X, Y and Z. The luminance information from the defect 5 further permits the approximate quantification of its size.

With a camera 4 operating at a frame rate of 25 images per second and a maximum speed of uniform movement of 5 cm per second, the defect 5 is thus moved by 2 mm per image.

The speed of uniform movement is linked to the frequency of acquisition of the images by the camera 4 and a compromise with the various illuminations implemented in the present invention permits the optimization of the quality of the images.

The images acquired when the transparent material 2 carried by the conveyor $3_1$ and $3_2$ is moving relative to the detection and localization station 1 permits, from one image to the next, the extraction of the information which is useful for analysis.

The luminance permits the separation of the defects 5 represented by dark spots from the bright background 7 serving as reference, the coordinates X, Y of the pixels representative of a defect 5 and thus of a dark spot, make it possible to determine the position of a defect 5 within the image, the movement of these pixels over a sequence of a plurality of images, for example about ten, allows a correlation of the information present in these images, and the excess intensities arising in the course of the encounter of the laser beam 13 with a defect 5 permit the calculation, by a computer, 24, of its depth within the material 2.

In order to separate the dark spots corresponding to the defects 5 from the bright background 7 as well as, possibly, the excess brightnesses due to the dust particles 11, the computer uses for example a method of calculation by adaptive threshold and/or of contour detection.

Moreover, from the multiple information gathered, the method monitors a defect 5 in the thickness of the material 2 represented by a point which is dark then bright as the defect 5 passes through the laser beam 13, and dust particles 11, represented by points which are brighter than the background 7 or embedded in the uniform contrast of the background 7, from one image to the next. Thus, the exploitation of the redundancy of information makes the detection of the defects 5 more reliable.

The image processing carried out by the computer is then locally focused on the presumed close zone surrounding the defect 5, in order to take into account its shape, its luminance etc. The fine analysis of this zone uses, for example, a prediction algorithm using a statistical correlation method.

The invention is not limited to the method and to the device for inspection as described in detail above. In particular, a description has been given of a conveyor on which there is entrained a transparent material to be inspected which moves in the vertical to an observation station. However, it is possible, without departing from the scope of the invention, to use a mobile observation station, the material to be inspected remaining fixed. This arrangement is in particular beneficial in the case of large parts to be inspected.

Furthermore, the white-light grazing illumination and the illumination of the bright background may be provided using light sources of a different nature from those of the invention, and likewise for the type of sensor utilized by the camera; a significant constraint to be obeyed being the provision of an overall illumination enabling the camera to distinguish a parasitic surface element from an inclusion.

Finally, it is entirely possible, without departing from the scope of the invention, to couple an identical second station in head to tail fashion to the detection and localization station so as to detect parasitic surface elements deposited on the lower face of the material.

We claim:

1. Method for inspecting transparent material by illumination by means of at least one light source, and by observation of the thickness of the material by at least one camera characterized comprising the steps of: uniformly illuminating with a first light source a bright background placed relative to the camera behind the material to be viewed by transparency through the material covering the field of view of the camera and serving as contrast reference:

laterally illuminating with a second light source the surface of the material by grazing said surface without substantially penetrating said material in order to distinguish defects included within the material from parasitic elements deposited on its surface and diffracting light;

viewing by transparency by the camera, placed in the vertical to the surface of the material, a sequence of contrasted images reproducing the thickness of the material; and processing information acquired by the successive images which are representative of the material seen in its thickness, to detect and locate the defects included within the thickness of the material corresponding to dark spots on the image.

2. Method according to claim 1, further comprising the steps of: illuminating by a laser beam passing trough the material in its thickness and inclined in relation to its surface; scanning to form a plane and oblique light curtain, in the field of view of the camera; and viewing by transparency, by the camera, a sequence of contrasted images reproducing successive sections of the material.

3. Method according to claim 1, wherein in order to process the information acquired by the images reconstructed by the camera the dark spots, corresponding to the defects included within the thickness of the material, are correlated with the excess light intensities produced by the laser beam encountering the inclusions.

4. Method according to claim 1, further comprising the steps of calculating the depth of the defects illuminated by the laser beam on the basis of their location relative to the 2 light strokes formed by the intersection of the laser beam with the transparent material to locate the defects in the 3 dimensions.

5. Method according to claim 1, wherein in order to view the successive sections of the material, the material is moved on a conveyor supporting the material in a horizontal plane beneath a fixed detection and location station.

6. Method according to claim 5, further comprising the steps of coupling an identical second station to the fixed first station in head to tail fashion in order to view the parasitic elements deposited on both sides of the transparent material.

7. Method according to claim 1, further comprises the steps of correlating the information on position of the defects which is acquired over several images.

8. Method according to claim 3, further comprising the steps of calculating the depth of the defects illuminated by the laser beam on the basis of their location relative to 2 light strokes formed by the intersection of the laser beam with the transparent material to locate the defects in the 3 dimensions.

9. Method according to claim 3, wherein in order to view successive sections of the material, the material is moved on a conveyor supporting the material in a horizontal plane beneath a fixed detection and location station.

10. Method according to claim 9, further comprising the steps of coupling an identical second station to the fixed first station in head to tail fashion in order to view the parasitic elements deposited on both sides of the transparent material.

11. Method according to claim 2, further comprising the step of correlating the information on position of the defects which is acquired over several images.

12. Method according to claim 3 further comprising the steps of correlating the information on position of the defects which is acquired over several images.

13. Device for inspecting transparent material by illumination and by observation of the thickness of the material by at least one camera comprising: at least one detection and location station including the camera placed in the vertical to the material to be inspected, to view a sequence of images representing successive sections within the thickness of the material, a uniformly illuminated bright background placed relative to the camera behind the material covering the field of view of the camera, an illumination source lateral to the material, which outputs a light beam to laterally illuminate a surface of said material by grazing said surface without substantially penetrating said material, said light beam being reflected by the surface of the material towards the camera, a laser illumination source coupled to means for expanding a laser beam emitted by the source in one single direction to form an oblique light curtain intended to illuminate successive sectional planes within the thickness of the material, and an image-processing computer for detecting and locating the defect within the thickness of the material.

14. Device according to claim 13, characterized in that the laser illumination source is placed relative to the camera behind the material in order to form the oblique light curtain.

15. Device according to claim 13, characterized in that the computer includes a device for calculating by adaptive threshold and/or for contour detection to separate dark spots from the bright background.

16. Device according to claim 13, characterized in that the computer includes a prediction device for the detection of defects on the sequential images by using a statistical correlation method.

17. Device according to claim 14, characterized in that the computer includes a device for calculating by adaptive threshold and/or for contour detection to separate dark spots from the bright background.

18. Device according to claim 14, characterized in that the computer includes a prediction device for the detection of defects on the sequential images by using a statistical correlation method.

19. Device according to claim 15, characterized in that the computer includes a prediction device for the detection of defects on the sequential images by using a statistical correlation method.

* * * * *